(12) United States Patent
Barthelaix et al.

(10) Patent No.: US 11,087,870 B2
(45) Date of Patent: Aug. 10, 2021

(54) SYSTEM AND METHOD OF TRACEABILITY OF A DENTAL PROSTHESIS, AND CORRESPONDING DENTAL PROSTHESIS

(71) Applicants: Universite D'Angers, Angers (FR); Centre Hospitalier Universitaire D'Angers, Angers (FR)

(72) Inventors: Annick Barthelaix, Asniere sur Vegre (FR); Jocelyn Rio, Angers (FR); Antoine Spiesser, Angers (FR)

(73) Assignees: UNIVERSITE D'ANGERS, Angers (FR); CENTRE HOSPITALIER UNIVERSITAIRE D'ANGERS, Angers (FR)

( * ) Notice: Subject to any disclaimer, the term of this patent is extended or adjusted under 35 U.S.C. 154(b) by 416 days.

(21) Appl. No.: 16/316,145

(22) PCT Filed: Jul. 7, 2017

(86) PCT No.: PCT/EP2017/067143
§ 371 (c)(1),
(2) Date: Jan. 8, 2019

(87) PCT Pub. No.: WO2018/007614
PCT Pub. Date: Jan. 11, 2018

(65) Prior Publication Data
US 2020/0327975 A1     Oct. 15, 2020

(30) Foreign Application Priority Data

Jul. 8, 2016  (FR) ...................................... 1656595

(51) Int. Cl.
*G16H 20/40* (2018.01)
*A61C 13/107* (2006.01)
(Continued)

(52) U.S. Cl.
CPC ......... *G16H 20/40* (2018.01); *A61C 13/0001* (2013.01); *G08B 5/36* (2013.01);
(Continued)

(58) Field of Classification Search
CPC ................ G16H 20/40; A61C 13/0001; A61C 2204/002; A61C 2204/005; A61C 13/00; G08B 5/36; G08B 21/24
See application file for complete search history.

(56) References Cited

U.S. PATENT DOCUMENTS 5,760,692 A * 6/1998 Block ................ G08B 21/0288
                                                 340/505
6,239,705 B1   5/2001 Glen
(Continued)

FOREIGN PATENT DOCUMENTS

CN     103247154 A     8/2013
CN     105302541 A1    2/2016
(Continued)

OTHER PUBLICATIONS

International Search Report dated Oct. 26, 2017 for corresponding International Application No. PCT/EP2017/067143, filed Jul. 7, 2017.
(Continued)

*Primary Examiner* — Toan N Pham
(74) *Attorney, Agent, or Firm* — David D. Brush; Westman, Champlin & Koehler, P.A.

(57) ABSTRACT

A system of tracing a dental prosthesis, the prosthesis including an electrical power source coupled with a radio-communications signals transmitter capable of assuming a weakly active state in which it periodically sends out signals at a first transmission frequency, and a highly active state in which it periodically sends out signals at a second, higher transmission frequency, and a presence sensor for sensing (Continued)

presence of the prosthesis in a mouth of a user, capable of delivering information on absence of the prosthesis in the mouth. The transmitter is configured to pass from the weakly active state to the highly active state when the sensor delivers information on absence of the prosthesis in the mouth. The system also includes a base forming a support of the dental prosthesis when not worn by a user, and the transmitter assumes the weakly active state on detecting the prosthesis in proximity to the base.

10 Claims, 4 Drawing Sheets

(51) Int. Cl.
   *G08B 5/36* (2006.01)
   *G08B 21/24* (2006.01)
(52) U.S. Cl.
   CPC ........ *G08B 21/24* (2013.01); *A61C 2204/002* (2013.01); *A61C 2204/005* (2013.01)

(56) References Cited

U.S. PATENT DOCUMENTS

| | | | |
|---|---|---|---|
| 9,632,532 | B2 | 4/2017 | Luna |
| 10,872,212 | B2 * | 12/2020 | Danaei-Moghaddam ................... A61C 13/01 |
| 2010/0289646 | A1 | 11/2010 | Raniere |

FOREIGN PATENT DOCUMENTS

| | | |
|---|---|---|
| WO | 9849660 A1 | 11/1998 |
| WO | 0213719 A1 | 2/2002 |

OTHER PUBLICATIONS

English translation of the International Written Opinion dated Oct. 26, 2017 for corresponding International Application No. PCT/EP2017/067143, filed Jul. 7, 2017.
English translation of the Chinese Office Action dated Jun. 2, 2020 for corresponding Chinese Application No. 201780047849.6.

* cited by examiner

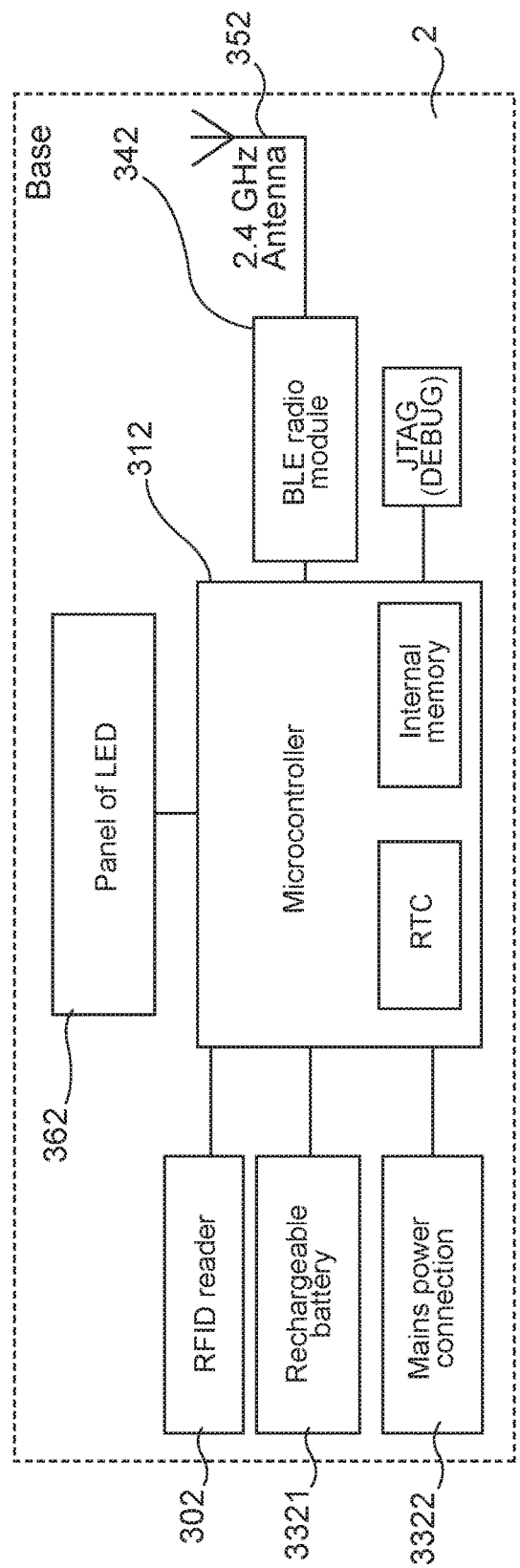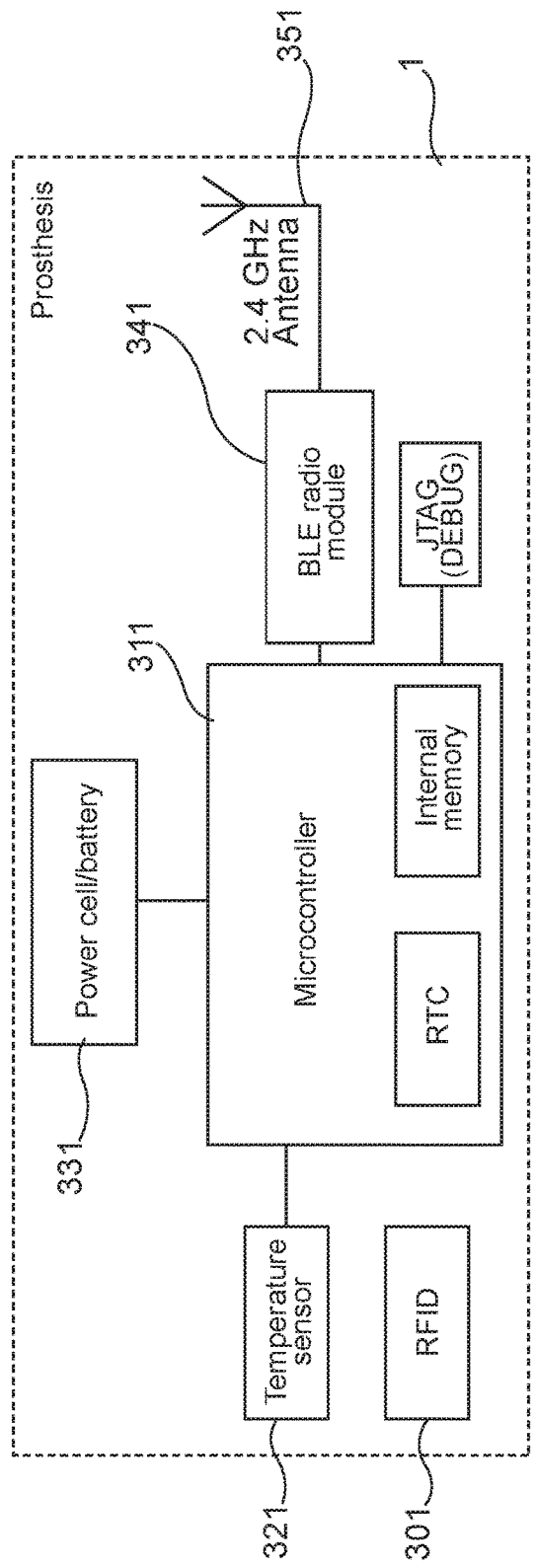

SYSTEM AND METHOD OF TRACEABILITY OF A DENTAL PROSTHESIS, AND CORRESPONDING DENTAL PROSTHESIS

CROSS-REFERENCE TO RELATED APPLICATIONS

This Application is a Section 371 National Stage Application of International Application No. PCT/EP2017/067143, filed Jul. 7, 2017, which is incorporated by reference in its entirety and published as WO 2018/007614 A1 on Jan. 11, 2018, not in English.

FIELD OF THE INVENTION

The field of the invention is that of dental prostheses (or dentures) and more particularly detachable dental prostheses, whether they are full prostheses or partial prostheses (hooked dentures). More specifically, the invention relates to the traceability of such dental prostheses, in terms of location, identification, and tracking of their maintenance, etc.

PRIOR ART AND ITS DRAWBACKS

Numerous difficulties associated with wearing removable dental prostheses are on record, especially but not exclusively among dependent individuals and more particularly but not only in institutional conditions.

Among these difficulties, a frequent problem is that of the loss of these prostheses which may be misplaced by their owners. While, at home, it may be a tedious task to search for the unexpected place in which the prosthesis might have been forgotten, this problem is much more complicated when the owner is in an institutional situation. Indeed, the area of search for the misplaced prosthesis is much greater. In addition, when a dental prosthesis is found, it may be difficult to identify its owner among all the inmates of the institution. Finally, this loss also raises problems of hygiene.

It can also be noted that poor care of the dental prosthesis can cause the ultimate loss of the prosthesis. Indeed, a poorly maintained dental prosthesis can cause oral lesions and injuries, pain or quite simply discomfort which can cause the patient to remove it and leave it at a more or less unexpected place.

Moreover, if the prosthesis and its owner are not quickly found, this loss can have major consequences in terms of cost of replacing the prosthesis (financial consequences) as well as in terms of comfort for the user, for whom the absence of prosthesis may cause eating difficulties of varying severity, nutritional deficiencies and also deterioration of self-esteem as well as of the person's appearance in front of others.

To overcome these various drawbacks, the patent document WO 02/13719 A1 proposes the insertion, into removable dental prostheses, of RFID type passive radiofrequency identification labels. Such labels memorize a code that can take the form of an identifier. They require no electrical power but use the energy of the magnetic signals received from a label reader to send out the code or the identifier that they contain. This identifier is then displayed on a screen of the reader, that can be connected to a database of the institution, correspondingly memorizing all the identifiers and the identification data of their owners.

In addition, such a portable reader can also be used to locate misplaced dental prostheses. To this end, the portable reader sends out an electromagnetic signal intended to excite the RFID label integrated into the dental prosthesis and comprises a receiver that detects the signal that the dental prosthesis sends out in response when it is situated within range of the portable reader.

This solution for identifying the owner of a misplaced prosthesis, while it is promising, is unsatisfactory for resolving the problem of locating a lost prosthesis. Indeed, the use of a chip called a passive chip, in the form of an RFID label, greatly restricts the field of search for this prosthesis since the range of the RFID label reader is limited to a few tens of centimeters. Thus, this technical solution is especially unsuited and insufficient in the particular example of a user living in an institutional environment who would have misplaced his dental prosthesis in the canteen and in whose case the healthcare staff would notice the loss of the dental prosthesis when he or she returns to their room.

In another field of application, the patent document U.S. Pat. No. 6,239,705 proposes an alternative technique in which an active chip is integrated into a dental prosthesis. This chip can send out longer range radiofrequency signals to enable the location of its owner. This solution does not seek to resolve the technical problem of the loss of dental prosthesis but that of locating their owners (who, it is assumed, still have their their prosthesis in the mouth), for military purposes especially. The dental prosthesis in this case also incorporates a power supply in the form of a power cell or battery to provide the energy needed for the active chip.

While this system offers greater range of location of the dental prosthesis, the use of an active radiofrequency transmitter raises the problem of autonomy of the power cell or battery that powers the active chip.

The patent document WO 98/49660 for its part proposes a dental prosthesis equipped with an active chip that can transmit a sound or light signal to assist in the location of the prosthesis when it is misplaced. To prevent the discomfort that could be caused to the wearer if the locating function is activated when the prosthesis is being worn in his or her mouth, the prosthesis is equipped with a presence sensor to sense presence in the mouth. Thus, when the sensor detects the fact that the prosthesis is in its user's mouth, the transmitter of sound or light signals remains inactive. The operation of such a sensor however also consumes energy.

There is therefore a need for a technique of traceability of a dental prosthesis that does not have these different drawbacks of the prior art.

In particular, there is a need for a technique of traceability of a dental prosthesis that enables the location of a misplaced dental prosthesis within a radius of about 10 meters or more. There is also a need for such a technique for easily identifying the owner of a found dental prosthesis. Finally, there is a need for such a technique that can propose a dental prosthesis that has energy autonomy of several months.

SUMMARY OF THE INVENTION

The invention meets this need by proposing a system of traceability of a dental prosthesis in which the dental prosthesis comprises a source of electrical power coupled with a transmitter of radio-communications signals capable of assuming a weakly active state in which it periodically sends out signals at a first transmission frequency, and a highly active state in which it periodically sends out signals at a second transmission frequency higher than the first transmission frequency. The prosthesis comprises at least one presence sensor for sensing the presence of the prosthesis in a user's mouth, capable of delivering a piece of information on the presence or absence of the prosthesis in the mouth, and the transmitter passes from the weakly active state to the highly active state when the sensor delivers a piece of information on absence of the prosthesis in the mouth. In addition, the system of traceability according to one embodiment of the invention comprises a base forming a support of the dental prosthesis when it is not being worn by a user. The transmitter is configured to assume the weakly active state on detecting a presence of the dental prosthesis in proximity to the base.

Thus, the invention relies on a wholly novel and inventive approach to the traceability of detachable dental prosthesis. Indeed, the dental prosthesis according to the invention integrates an electrically powered active chip comprising a radio-communications signals transmitter that can send out signals of a range of about ten meters when the dental prosthesis is misplaced. Such a dental prosthesis therefore efficiently resolves the problem of the location of misplaced prostheses, especially in institutional settings, through a radio-communications signals transmission range far greater than it is according to the prior art techniques relying on the use of passive radiofrequency identification labels.

In addition, this radio-communications signals transmitter is advantageously coupled with a presence sensor for sensing the presence of the dental prosthesis in its user's mouth. Thus, the transmitter does not send out radio-communication signals at a high and therefore energy-intensive transmission frequency, enabling the location of the dental prosthesis, unless it is truly misplaced, i.e. when the presence sensor detects that the prosthesis is no longer in its user's mouth.

Thus, the electrical consumption related to the sending of radio-communications signals at high frequency by the dental prosthesis is strictly limited to periods during which the prosthesis has been misplaced, thus enabling satisfactory energy autonomy for the dental prosthesis, for example autonomy of several months.

In addition, such a system of traceability comprises a base forming a support for the dental prosthesis when it is not being worn by a user. The dental prosthesis is thus advantageously matched with a base on which the user must place his removable dental prosthesis as soon as he is not wearing it: this support is a preferred place for storing the dental prosthesis, and prevents it from being misplaced through being put down in an incongruous place when the user removes it from his mouth.

To further reduce the energy consumption of the prosthesis and thus increase its autonomy, the radio-communications signal transmitter of the prosthesis remains in a weakly active state so long as it is situated in proximity to the base. It will be noted that, in one alternative embodiment, this weakly active state is an inactive state in which the first sending frequency is zero and the transmitter of the prosthesis does not send out any signals.

According to one embodiment, the prosthesis is configured so that, on detection of a presence of the dental prosthesis in proximity to the base, it operates in "base" mode in which the presence sensor is in an inactive state and the radio-communications signal transmitter is in a weakly active state.

Thus, the energy consumption of the dental prosthesis is greatly reduced. Indeed, when the dental prosthesis is positioned on its base, it is not necessary for the presence sensor to carry out measurements of the presence of the prosthesis in its user's mouth. The transmitter can also be weakly active or even in one variant it can be inactive. Thus, when an exchange of requests and responses between the transmitters/receivers of the base and of the prosthesis confirms the presence of the dental prosthesis on its support, it is possible to deactivate these two elements. According to a first embodiment, it is the base that sends a command for deactivating these two elements to the dental prosthesis. According to a second embodiment, it is the prosthesis that manages the deactivation of these two elements, on receiving a response from the base to a request that this prosthesis has made to it. The energy consumption of the dental prosthesis is therefore greatly reduced, extending the autonomy of the electrical power source of the prosthesis.

According to one embodiment, on detecting an absence of the dental prosthesis in proximity to the base, the dental prosthesis is configured to work in "recognition" mode in which the presence sensor carries out a measurement of presence at a determined frequency, and in which the radio-communications signal transmitter is in the weakly active state.

Thus, as soon as it is detected that the dental prosthesis is at a distance from the base, the presence sensor is activated so that it carries out regular measurements of the presence of the prosthesis in its user's mouth. Indeed, when the dental prosthesis leaves the base, the most probable scenario is that it is placed in its user's mouth: it is then necessary to regularly verify this presence of the prosthesis in the mouth. The radio-communication signal transmitter can, on the contrary, remain in a weakly active state to reduce energy consumption of the prosthesis so long as the sensor does not deliver any information on absence of the dental prosthesis from its user's mouth.

The frequency of the measurements made by the presence sensor can be permanently set during the designing of the prosthesis, or then cay be made adjustable, for example in order to adapt to the prosthesis owner's habits, or to optimize the energy consumption of the sensor.

According to one embodiment, the transmitter is configured so that, when the sensor delivers a piece of information on absence of the prosthesis in the mouth, it passes from the weakly active state to the highly active state in which it is configured to periodically send out signals at a second transmission frequency. The base comprises a module for sending a command for a mode of operation of the dental prosthesis that is configured to send to the dental prosthesis, upon a user's action, a command for operation in "location" mode, in which the radio-communication signals transmitter is configured to periodically send out signals at a third transmission frequency higher than the second transmission frequency.

Thus, as soon as the presence sensor reports that the dental prosthesis is no longer in the user's mouth, the radio-communications signals transmitter passes into a highly active state and periodically, but at a relatively low frequency, sends out radio-communications signals (for example a BLE frame every two minutes). Thus, the energy consumption of the transmitter is reduced so long as the user is not in a phase of actively searching for the misplaced dental prosthesis. Indeed, the dental prosthesis may have left the user's mouth but is not necessarily misplaced (for example it may be in the course of being cleaned).

However, as soon as the user (i.e. the owner of the prosthesis or someone close to him or a healthcare person) notices that the prosthesis has been misplaced, and wishes to locate it, he or she can activate a "location" mode, for example by actuating a button provided on the base. The base then sends out a command for passage into "location" mode in which the radio-communications signals transmitter of the prosthesis will send out signals more frequently (for example one BLE frame every 30 seconds) to enable the base to rapidly locate the misplaced prosthesis.

The second and third transmission frequencies for radio-communication signals from the dental prosthesis are preferably chosen to obtain a compromise between a speed of location of the misplaced prosthesis and control over the energy consumption of the dental prosthesis.

The base with which the dental prosthesis is matched can therefore manage the operating mode of the components of the dental prosthesis, and especially the presence sensor and the radio communications signals transmitter by sending them commands, for example according to the Bluetooth® LowEnergy (BLE) or Bluetooth Smart® standard.

According to one embodiment, such a base comprises a warning module configured to send out an alert:
- when a duration of presence of said dental prosthesis in proximity to said base is greater than a determined threshold of presence, or
- when a duration of absence of said dental prosthesis in proximity to said base is greater than a determined threshold of absence.

Thus, the base advantageously enables a tracking of the hygiene of the dental prosthesis and of its use by its owner.

Indeed, when the prosthesis remains far too long on the base, this can mean that the dental prosthesis is not being sufficiently worn by the user: the duration of presence can be measured between two successive instances of remoteness (or distancing) of the dental prosthesis from its support, or it can be evaluated in a totalized form over a given period of observation (for example, the totalized duration of presence of the dental prosthesis on its base in the course of a week).

Similarly, if the period between two successive repositioning operations for repositioning the dental prosthesis on its base is far too lengthy, it can mean that the user is not sufficiently taking care of his dental prosthesis.

In each of these two cases, the oral consequences for the user of the dental prosthesis can be harmful, and it can therefore be necessary to send out an alert or warning message. This alert can be sent out directly by the base. As a variant, the base can send back this information on tracking the duration of presence or absence to a server which can broadcast these alerts to a smartphone or to a tablet belonging to concerned individuals (for example the healthcare staff or the user's family and friends). When the dental prosthesis is not being sufficiently worn, this can be a result of discomfort for the user or even injury of the oral mucous membranes prompted by the dental prosthesis. The warning message sent out can then advantageously be associated with advice given to the user or to his friends and family on the settings of the dental prosthesis to be made in a dental clinic (setting or adjustment of the dental bite, relining/readjusting of the resin in contact with the tissues etc.).

According to one embodiment, the base comprises a unit for locating the dental prosthesis, comprising at least one directional antenna connected to a radio module capable of receiving the radio-communications signals sent out by the transmitter of said dental prosthesis and a set of light and/or sound indicators for controlling a direction of reception of said signals.

Thus, the base can advantageously be used as a device for locating the misplaced prosthesis. To this end, it is preferably equipped with a rechargeable battery enabling energy autonomy during these phases of searching for the prosthesis. In addition, it is equipped with one or more directional antennas, for example in the form of a network of antennas, enabling it to pick up the radio-communications signals sent out by the misplaced dental prosthesis and identify its direction of transmission. This radio antenna or these radio antennas can for example take the form of ceramic patches. In addition, the base preferably has a set of light indicators, for example in the form of a panel of LEDs, making it possible to assist the user in his search for the prosthesis, in displaying the direction of reception of the signals coming from the prosthesis. As a variant, sound beeps can be sent out by the base, for example at a frequency variable according to the orientation of the base relative to the prosthesis: a frequency of the sound beeps sent out by the base will increase when the base is pointed in the direction of the misplaced dental prosthesis.

According to one embodiment, the base comprises a module for charging said electrical power source by induction.

Thus, re-positioning the dental prosthesis on its base enables the recharging of the battery embedded in the prosthesis.

According to one embodiment of the invention, the sensor is a temperature sensor that delivers information on absence when the measured temperature is below about 35° C.

Indeed, so long as the prosthesis is in the user's mouth, the temperature measured by the presence sensor is appreciably equal to the temperature of the human body, i.e. of the order of 37°. A drop in this measured temperature can indicate that the dental prosthesis is no longer in its user's mouth but has been misplaced, for example forgotten on a food tray in the canteen.

In other embodiments of the invention, such a presence sensor can for example be a moisture sensor: indeed, so long as the dental prosthesis is in the mouth, it is in contact with the user's saliva, hence in a moist environment. A drop in the hygrometry values measured by the presence sensor can also indicate that the dental prosthesis is no longer being worn by its user, and that it can therefore have been misplaced.

According to one embodiment of the invention, the dental prosthesis comprises a passive radiofrequency identification label and the base comprises a radiofrequency identification label reader capable of detecting a presence or an absence of the dental prosthesis in proximity to the base.

Such an RFID label preferably comprises data for identifying the dental prosthesis and its user such as for example:
- an identification number of the dental prosthesis;
- the family name/first name of its owner, as well as his social security number;
- in the case of persons living in an institutional environment, the room number of the owner of the prosthesis.

When the base reads the information contained in the RFID label of the prosthesis, this information can be displayed on the screen provided on the base or on the screen of a computer, a tablet or a smartphone to which the base is connected.

This makes it possible to verify the identity of the owner of the dental prosthesis, which can prove to be particularly useful when the dental prosthesis has been lost and then found again in a collective structure (hospital center, retirement home, an accommodation center for elderly dependent persons (in French "établissement d'hébergement pour personnel âgées dépendantes" or EHPAD etc.).

The invention also relates to a dental prosthesis comprising an electrical power supply source coupled with a radio-communications signals transmitter capable of assuming a weakly active state in which it periodically sends out signals at a first transmission frequency and a highly active state in which it periodically sends out signals at a second transmission frequency higher than the first frequency. Such a prosthesis comprises at least one presence sensor for sensing presence in a user's mouth capable of delivering a piece of information on presence or absence of the prosthesis in the mouth; the transmitter is configured to pass from the weakly active state to the highly active state when the sensor delivers a piece of information on the absence of the prosthesis in the mouth, and to assume the weakly active state on detecting a presence of the dental prosthesis in proximity to a base forming a support of the dental prosthesis when it is not being worn by a user.

The invention also relates to a method of traceability of a dental prosthesis, implemented in the system of traceability described here above.

LIST OF FIGURES

Other aims, features and advantages of the invention shall appear more clearly from the following description, given by way of a simple illustrative and non-exhaustive example with reference to the figures, of which:

Figure 1:
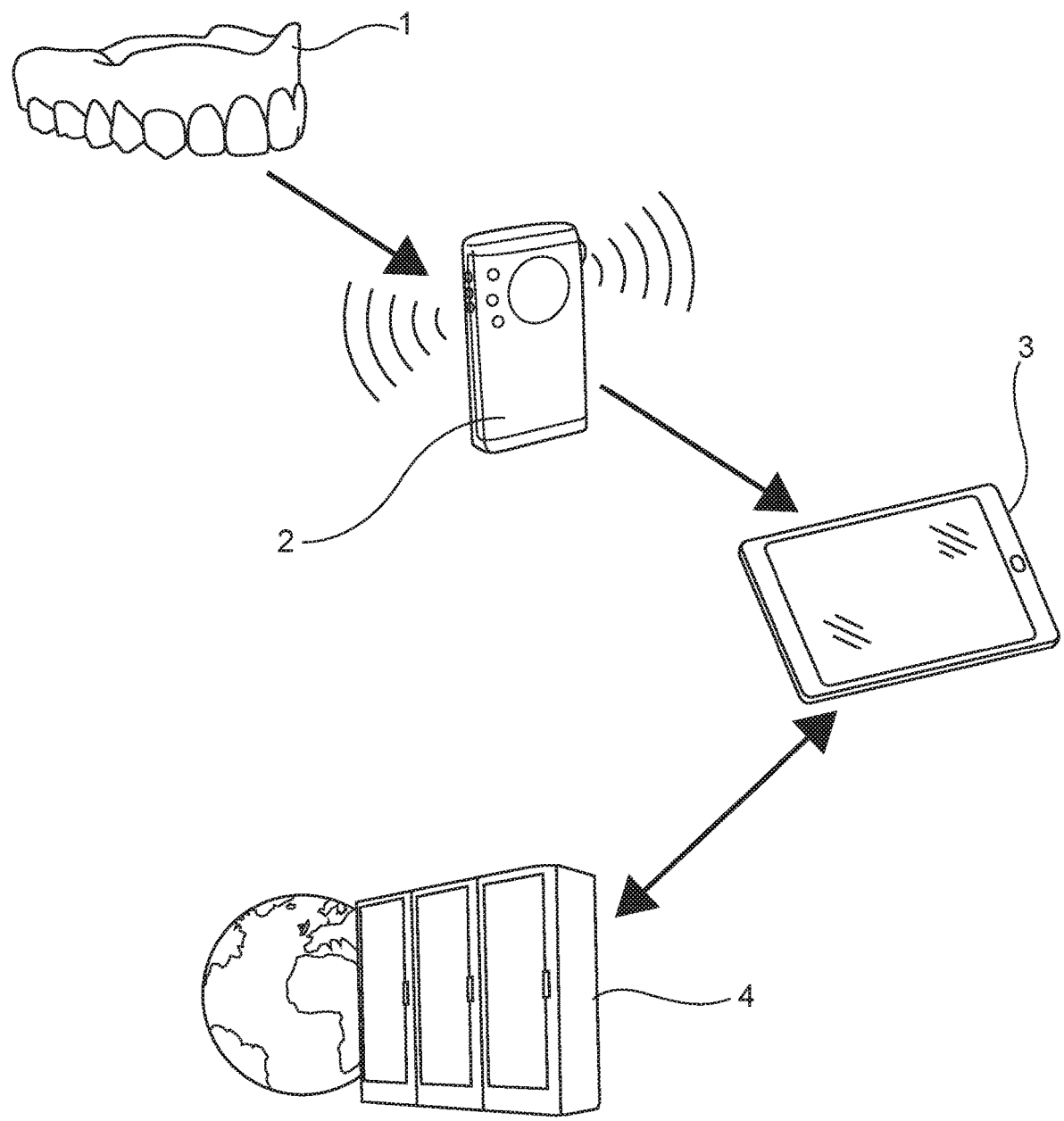
FIG. 1 is a block diagram of the system of traceability of dental prosthesis according to one embodiment of the invention.
Figure 5:
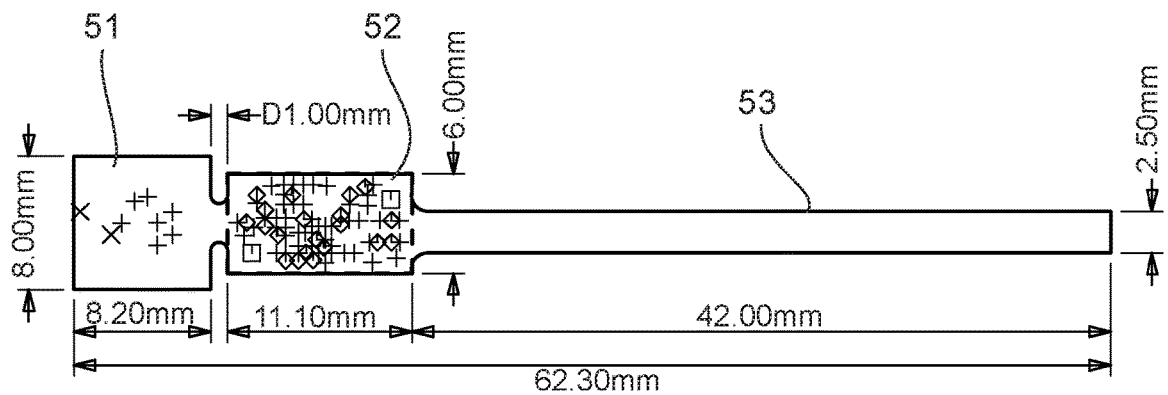
Figure 4:
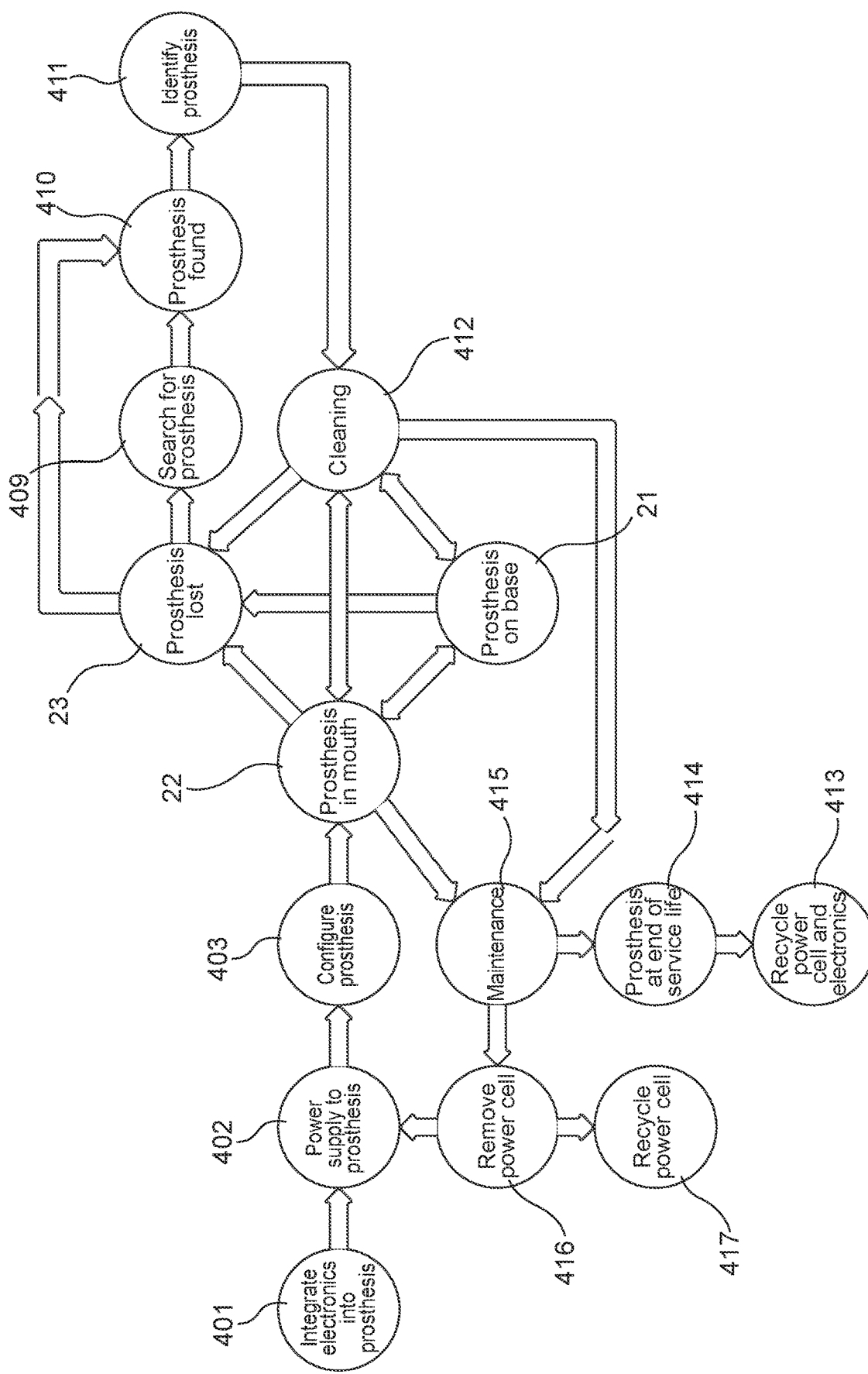

FIGS. 3A and 3B respectively represent functional block diagrams of the electronic modules embedded in the dental prosthesis (FIG. 3B) and in the base forming the support of the prosthesis (FIG. 3A);

FIG. 4 presents, in the form of state graphs, the different states and modes of operation of the system of FIG. 1;

FIG. 5 illustrates an example of a shape of a printed circuit to be integrated into the dental prosthesis according to one embodiment of the invention.

DETAILED DESCRIPTION OF EMBODIMENTS OF THE INVENTION

The general principle of the invention relies on the coupling, in a removable dental prosthesis, of an active radio-communications signals transmitter (i.e. powered by an electrical power supply source, as opposed to an RFID type passive transmitter), and a presence sensor for sensing the presence of the dental prosthesis in a user's mouth that makes it possible not to make the radio-communications signals transmitter work in energy consumption mode unless it is detected that the dental prosthesis is no longer in its user's mouth and is therefore potentially misplaced.

Referring now to FIGS. 1 to 4, we present the system and the method of traceability of dental prosthesis according to different embodiments of the invention.

As illustrated in FIG. 1, such a system of traceability comprises a removable dental prosthesis 1 which can be a total or partial (hooked) prosthesis. As shall be described in greater detail here below with reference to FIG. 3B, such a dental prosthesis 1 embeds electronic components and especially a microcontroller type active chip, as well as an associated electrical power supply source. In one embodiment, it also integrates an RFID type passive radiofrequency label. The different components enable both the identification and the location of the dental prosthesis 1 as well as the traceability of the actions and maintenance performed on the prosthesis 1 but also the communications of the prosthesis 1 with an interface of the smartphone or tablet (3) type.

Such communication with a smartphone or a tablet 3 is carried out by means of a reader 2, comprising a receiver capable of receiving the radio-communications signals sent out by means of the active chip of the dental prosthesis 1. In one optional embodiment, the reader 2 also comprises an RFID type radiofrequency label reader capable of reading information contained in the RFID label of the prosthesis 1 when it is situated in proximity to this prosthesis.

In one embodiment of the invention, the reader 2 is constituted by a base forming a support of the dental prosthesis 1 when it is not worn by its user. As a variant, the reader 2 can be a portable reader distinct from the base but capable of communicating with it. The reader 2 can also be integrated into a mobile radio-communications device such as a smartphone or a tablet.

The reader 2 can be in communication, through Bluetooth® type signals for example, with the communication support 3 of the smartphone or tablet type, or even companion robot type in the case of dependent individuals or individuals with reduced cognitive abilities. A software application can be developed and executed on the communications support 3 to form an interactive hinge with the wearer of the dental prosthesis 1 and/or his or her friends and family.

Such communications can be envisaged on several levels:

the communications support 3, or the reader 2 itself (although not illustrated in FIG. 1) can send the information up to a server 4. Since the management of data relating to the health of individuals is subject to data protection regulations, such a server 4 is a certified server enabling the storage of data coming from the communications support 3 (such as data from the patient's medical file), access to this data, its communication, its exchange in compliance with the CNIL (Commission Nationale Informatique et Liberté or National Commission for Data Protection and Liberties established under French Law on Mar. 4, 2002). Such a transfer of information towards the server 4 can be done with a certain periodicity, for example whenever the dental prosthesis 1 is resting on the reader 2 forming a support. In particular, the server 4 can thus determine the duration that has elapsed between two successive positions of the dental prosthesis 1 on its base 2. If this duration is far too great, it can mean that the patient is not taking sufficient care of his prosthesis, and this may be harmful in terms of hygiene and lead to the appearance of oral lesions. The server 4 can also determine the duration of positioning of the dental prosthesis 1 on the base 2: if this duration is far too great, it can mean that the prosthesis 1 is not being sufficiently worn by its user, and this may be related to discomfort or even an area of injury on the oral mucous membranes, caused by the dental prosthesis 1. The server 4 can then send advice, displayed on the screen of smartphone or tablet 3 and consulted by the user of the prosthesis and his or her family and friends, on the adjustments of the dental prosthesis 1 to be made in a dental clinic (adjustment of the dental bite, relining of the base/readjustment of the resin in contact with the tissues etc.). The server 4 can also send an alert to the base 2 which can emit flashing lights or emit a sound signal to report this malfunction or this misuse of the prosthesis;

the communications support 3 can enable access the user of the prosthesis 1 or his family and friends to obtain access to an informative database stored on the server 4. Such informative data can relate to the maintenance of the prosthesis (hygiene states, types of products, brushing methods etc.), appointments for checks and adjustments type of food to be adapted according to the type of prosthesis, stabilizing means (adhesive, fixing means etc.), ways to make the dental prosthesis more comfortable, methods of adapting to a new dental prosthesis 1 during the first day of its use etc.

the communication support 3 can also enable access to information stored on the server 4, pertaining to the manufacture of the dental prosthesis 1 (ISO or International Standardization Organization standards, types of materials, prosthetic laboratory etc.).

Here below, referring to FIGS. 1 and 3A-3B, we present the principle of operation of the system of traceability of FIG. 1 when a removable dental prosthesis 1 has been misplaced.

FIG. 1 illustrates the three main positions of the removable dental prosthesis 1:

position 21: positioned on its base 2 forming a support of the prosthesis 1, when this prosthesis is not being worn by its user, for example at night;

position 22: in its user's mouth;

position 23: misplaced by its user.

In the position referenced 21, the BLE (Bluetooth LowEnergy®) radio module 342 (see FIG. 3A) integrated into the base 2 can send a request for obtaining identification data of the prosthesis 1 and/or the patient to the microcontroller 311 of the prosthesis 1 (see FIG. 3B): these pieces of data are stored directly in the internal memory of the microcontroller 311 and can be transmitted to the base 2 by the BLE radio module 341 of the prosthesis 1. These pieces of data make it possible to record an identification of the owner of the prosthesis (serial number such as the social security number for example or family name/first name).

In one variant implementing an RFID passive radiofrequency label 301, in the position referenced 21, the radiofrequency label reader 302 (see FIG. 3A) integrated into the base 2 enables a short-distance reading of the RFID label 301 (see FIG. 3B) integrated into the dental prosthesis 1: this reading enables access to these same pieces of identification data.

Thus, when a misplaced dental prosthesis 1 is found, it is possible, by positioning it on a base 2, to verify the identity of its owner. This is particularly useful in the event of loss in a collective structure (an institution, EHPAD home or hospital for example).

In addition, such an exchange of (request and response) data frames between the base 2 and the prosthesis 1 make it possible to provide the base 2 with information on the presence, in proximity, of the dental prosthesis 1. The base 2 then detects the fact that the dental prosthesis 1 must work in "base" mode in which the temperature sensor 321 must be in an inactive state in order to reduce the energy consumption of the dental prosthesis 1. In this operation, in "base" mode, the transmitter 341 of the prosthesis 1 also shows very little activity and for example sends only one BLE frame every 15 minutes approximately in order to confirm its presence in proximity to the base 2. Its energy consumption is therefore also very low so as to preserve the energy autonomy of the prosthesis 1.

Indeed, a major problem of this type of system of traceability of a dental prosthesis is that of obtaining sufficient energy autonomy for the prosthesis, for example between two successive appointments for dental care to the dentist, most often at intervals of six months. It is therefore particularly important, in one embodiment where the electrical power source 331 (cells or batteries) is not rechargeable, to achieve fine control of the electrical consumption of the components illustrated in FIG. 3B. To this end, the transmission power of the BLE radio module 341 will for example be limited to a power value of 0 dBm.

Figure 2:
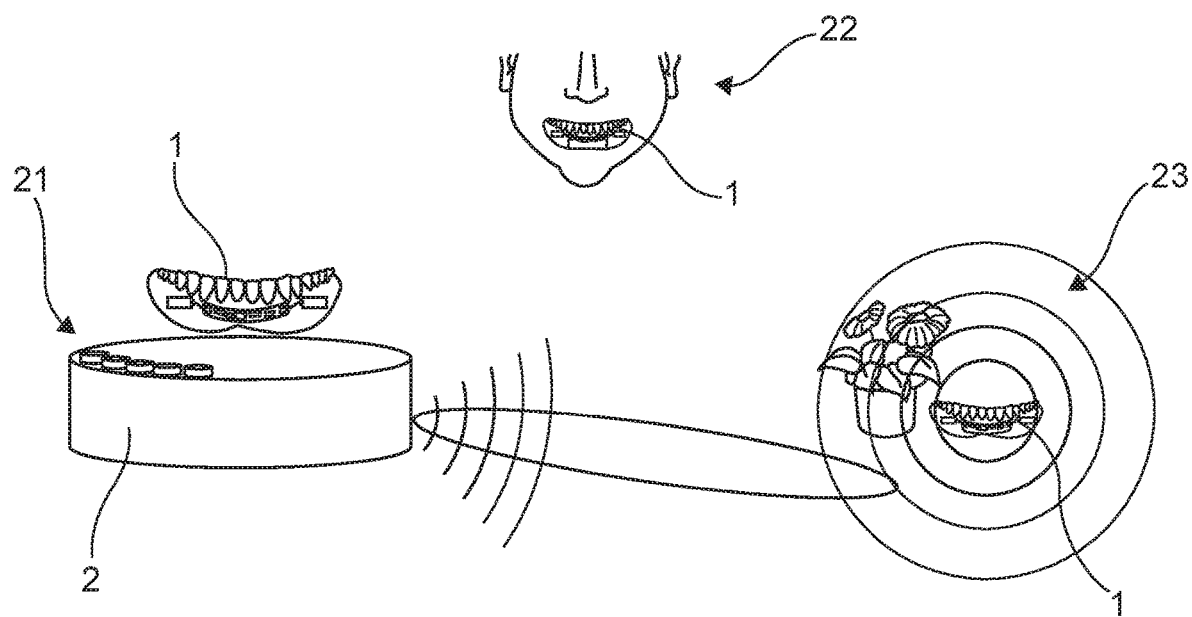
FIG. 2 illustrates a mode of operation of a system of FIG. 1 when a dental prosthesis is misplaced.

In this "base" mode, when the dental prosthesis 1 is in the position referenced 21 in FIG. 2, the energy consumption of the prosthesis 1 is therefore reduced to the minimum: the transmission of radiofrequency signals is very infrequent and no measurement of temperature is made. As a variant, the transmitter 341 of the prosthesis can even be totally deactivated and the microcontroller 311 can be in standby mode.

When the BLE radio module 341 no longer receives any response from the base 2 to the frames sent out, the microcontroller 311 then detects the fact that the dental prosthesis is no longer positioned 21 on its support. The most probable assumption then is that the dental prosthesis 1 has passed into the position 22 in its user's mouth.

The microcontroller 311 then drives or manages a changing of the operation of the dental prosthesis 1 into "recognition" mode. As a variant, it is the microcontroller 312 that drives or manages the transmission, by the BLE radio module ((Bluetooth LowEnergy®) 342, of a command signal intended to make the dental prosthesis 1 pass into "recognition" mode. This control signal is sent out by the directional antenna 352 of the base 2 and received by the antenna 351 of the prosthesis 1, then decoded by the BLE radio module 341 of this prosthesis 1.

In this "recognition" mode, the microcontroller 311 of the dental prosthesis 1 then drives the activation of the temperature sensor 321 of the dental prosthesis 1, and a measurement of temperature is then carried out at regular time intervals (for example every five or ten minutes) by the temperature sensor 321. The BLE radio module 341 of the prosthesis 1 continues to send out BLE frames at time intervals that are regular but very spaced out, for example every 15 minutes.

It will be noted as a variant that the temperature sensor 321 can be replaced for example by a moisture sensor. Similarly, as a variant, the radio modules 341 and 342 of the base 2 and of the prosthesis 1 can also use communications protocols other than BLE, which however has the advantage of a satisfactory range of 20 to 30 meters, a relatively low transmission power and satisfactory energy consumption. It is however also possible to envisage the use of radio-communications protocols of the Wi-Fi® type (although they have a higher energy consumption than BLE), NFC (Near Field Communication) type or active RFID type (these last two protocols however have the drawback of excessively limited range and/or the need to transmit at multiple frequencies).

When the temperature measured by the sensor 321 is above a configurable temperature threshold (for example 35° C.), the prosthesis 1 is considered to be worn by its owner (position 22) and the "recognition" mode remains engaged. The BLE radio module 341 then works in a low energy consumption mode in which the frequency of transmission of the data frames to the base 2 is low. As a variant, in this "recognition" mode, the radio function of the BLE radio module 341 is deactivated.

When the temperature measured by the sensor 321 falls below a certain threshold (for example 35° C.), it is assumed that the prosthesis 1 may be misplaced (position 23). The microcontroller 311 of the dental prosthesis 1 then drives the passage of the prosthesis 1 into "listening" mode in which the radio function of the BLE radio module 341 is activated but maintained at limited energy consumption (for example one BLE frame is transmitted every 2 minutes instead of 5 frames in the "recognition" mode), pending reception of information from the base 2.

When the owner of the prosthesis 1 or a person close to him or her detects the fact that the prosthesis 1 has been misplaced (position 23), this person actuates a button or a switch provided for this purpose on the base 2. In one variant, this activation cannot be done directly on the base 2 but by means of an application executed on a mobile phone of a smartphone or tablet type. The microcontroller 312 of the base 2 then drives the transmission, by the BLE radio module 342 and via the directional antenna 352, of control signals intended for the prosthesis 1 to make it pass into "location" mode. In this mode of operation, the BLE radio module 341 of the prosthesis 1 is active and periodically sends radio communication signals that are intended for the base 2 searching for the prosthesis 1 and that can be picked up by the directional antenna 352 of the base 2 (for example one BLE frame every 30 seconds). The strength of the signal received by the base 2 is measured and correlated with a distance and a direction to enable the geolocation of the misplaced prosthesis 1.

The directional antennal 352 of the base is for example a ceramic patch type antenna or one or more (2 or 4) antennas placed in a network. As a variant, the directional antenna 352 can consist of a network of patch type antennas on PCB (Printed Circuit Board).

As illustrated in FIG. 3A, the base 2 works on mains power 3322 and integrates a rechargeable battery 3321 enabling the power supply to the base 2 when it is travelling, when the user is searching for the misplaced prosthesis.

When the signal sent out by the BLE radio module 341 of the prosthesis 1 is detected by the directional antenna 352 of the base 2, without any movement by the user, a rotational movement operated by the user optimizes the strength of the received signal and therefore gives the indication of its direction of reception. The movement of the user makes it possible to inform him that he is approaching or moving away from the target formed by the misplaced prosthesis. A panel of light indicators 362 facilitates the search: for example, the panel of illuminated light indicators increases when the user points the base or the portable reader 2 towards the reception of the signal coming from the prosthesis 1. As a variant, the panel of light indicators 362 can be replaced by a speaker emitting sound beeps that get increasingly close to each other in time as and when the base 2 points towards the misplaced prosthesis 1. This variant is particularly advantageous in searches for the prosthetic device made by a visually impaired person, whose investigations can be guided efficiently by this sound accompaniment.

When the user, following the direction indicated by the base 2, recovers the misplaced dental prosthesis 1, he places it on the base 2 in order to read the identification data that it contains and verifies the identity of the retrieved prosthesis. If the retrieved prosthesis 1 truly corresponds to the prosthesis 1 that is being searched for, an exchange of success messages between the microcontroller 312 of the base 2 and the microcontroller 311 of the prosthesis 1, through the BLE radio modules 341 and 342, makes the prosthesis 1 pass back into "base" mode in which the presence sensor 321 is in an inactive state, and the microcontroller 311 is in a low energy consumption state, driving the very low frequency transmissions of data frames by the BLE radio module 341.

The passage into "base" mode can be done at the initiative of the microcontroller 311 of the dental prosthesis 1, upon detection of a response from the BLE radio module 342 of the base 2 to a request sent out by the BLE radio module 341 of the dental prosthesis 1. It can also be managed or driven by the BLE radio module 342 of the base 2, which sends out a command signal for the operation of the dental prosthesis 1 in "base" mode: upon reception of this command signal, the microcontroller 311 of the prosthesis drives the deactivation of the presence sensor 321 and reduces the frequency of transmission of data frames by the BLE radio module 341 to one frame every 15 minutes approximately.

If the prosthesis 1 is far too distant from the base (typically beyond 25 meters), no signal is detected by the base 2. A warning message (light indicator, flashing light, sound alarm) is broadcast on the base 2 when the user has initiated the passage into "locating" mode to inform him of this situation. The user can then move the base 2 until it is within radio range of the misplaced prosthetic device.

The different electronic components of the prosthetic device 1 illustrated in FIG. 3B can be disposed in several locations (three for example) of the dental prosthetic device 1 as illustrated in FIG. 5. The available volume of each housing can be of the order of 1 cm×0.5 cm×3 mm and these different zones or housings can be connected to one another by wire connections. These housings are made in the dental prosthetic laboratory: the prosthodontist does a drilling into the mass of resin of the prosthetic device, positions the electronic devices and seals them into their respective cavities by adding a self-polymerizing or light-polymerizing fluid resin so as to isolate the electronic components of moist and bacterial oral environment. The power cells 331 can consist for example of two PR63 power cells with a diameter of 5.8 mm and a thickness of 2.1 mm.

The diagram of FIG. 5 illustrates an example of a shape of the printed circuit to be integrated into the dental prosthesis. Such a printed circuit comprises three zones referenced 51 to 53. The zones referenced 51 and 53 are preferably flexible, especially the long zone referenced 53 which is particularly flexible. The cross-shaped and square-shaped symbols illustrate the layout of the electronic components which are present on the zones referenced 51 and more particularly 52. Thus, the presence of large numbers of components in the central zone 52 stiffens this part of the printed circuit. The dimensions in millimeters mentioned for the diagram of FIG. 5 give an indication of the real size of such a printed circuit.

In one alternative embodiment, the electrical power source 331 of the dental prosthetic device is rechargeable. For example, it is recharged by induction when the prosthetic device 1 is positioned on the base 2, for example at night after the denture has been cleaned.

In addition, the base 2 can take the form of a depleted-charge indicator for the power cell or battery 331 to alert the user of the prosthetic device to the need to recharge or change the power cell or the battery 331. For example, such an indicator is a light indicator which lights up green when the level of charge of the power cell or battery 331 is greater than or equal to 30%, orange when it is from 15% to 30% and red when it goes below 15%.

As a variant, the microcontroller 311 of the prosthetic device can activate the sending of a signal indicating depleted charge in the power cell or battery 331 to the smartphone or tablet 3 in order to warn the user or family and friends that the level of charge of the cell or battery 331 is low.

The base 2 can also be equipped with a counter or a clock to evaluate the time remaining before the next check and maintenance appointment with the prosthodontist or dental surgeon. Such appointments must generally take place every three months approximately. In one embodiment, when the counter of the base 2 indicates that there is only one month left before the next check and maintenance appointment, the microcontroller 312 of the base 2 activates the transmission of an alert or warning signal to the smartphone or the tablet 3 to warn the user or his family and friends that it is time to make an appointment with the prosthodontist or the dental surgeon. Such an appointment with the dental prosthodontist can be the opportunity to replace the fuel cell 331 of the prosthetic device 1 and to reset the counter/clock of the base 2. As a variant, the alert is directly sent out by the base 2 on a dedicated screen or by lighting up a light indicator or again by sending out a sound message.

FIG. 4 presents a view, in the form of state diagrams, of the different possible states of the system of traceability according to one embodiment of the invention. In this figure, the different arrows indicate the possible passages from one state to another. More particularly:

the state referenced 401 corresponds to the integration of all the electronic components of FIG. 3B into the dental prosthetic device 1;

at the end of the state referenced 401, the operation passes into the state referenced 402 in which the dental prosthetic device is powered electrically, for example by insertion of the power cell 331;

from there, it is possible to carry out the configuration 403 of the prosthetic device, for example by the storage, in the RFID label 301 or in the internal memory of the microcontroller 311, of the data identifying the owner of the prosthetic device (social security number, family name/first name etc.) and by the storage, in the internal memory of the microcontroller 311, of the program code instructions needed for the working of the system of traceability of the invention;

after configuration 403 of the prosthesis, it can pass into the state referenced 22 where it is situated in its owner's mouth;

from this state 22 where the prosthesis is in the mouth, different scenarios can be envisaged:

the prosthesis 1 can pass to the state 21 where the prosthesis is positioned on its base 2;

the prosthesis 1 can be misplaced (state referenced 23);

the prosthesis 1 can pass into a state 412 of cleaning (brushing, placing in a glass of water with possible addition of cleansing products etc.);

finally, the prosthesis 1 can go back into a state 415 of maintenance with the prosthodontist, for example for a setting or an adjustment of the prosthesis 1 to its user's morphology.

From the state 21 where the prosthesis 1 is on its base 2, it is also possible to pass into the state 22 where the prosthesis is in the mouth, or into the state 412 of cleaning the prosthesis or again into the state 23 where the prosthesis is lost. When the prosthesis 1 leaves the state 21, the presence sensor goes into the active state.

It is also possible to pass directly from a state 412 of cleaning the prosthesis 1 to a state 415 for maintenance with the prosthodontist. At the end of cleaning 412, there is also the possibility of losing the prosthesis (state 23).

When the prosthesis is lost (state 23) it can be directly found again by its user (state 410), for example because it is visually accessible to the user. If the user does not locate it, he can use the base 2 to launch an active search 409 for the dental prosthesis.

In any case, when the dental prosthesis is recovered (state 410), it is desirable to identify its owner (state 411) by reading data contained in the RFID label 301 of the prosthesis, or to obtain this data stored in the microcontroller 311 in response to a request sent out by the BLE radio module 342 of the base 2. This access to the identification data of the prosthesis and/or of the patient can be done by means of the base 2 or a dedicated portable reader or again by means of a smartphone or of a tablet equipped with an RFID reader. It is also possible to envisage a case where the RFID label or the internal memory of the microcontroller 311 contains only one identification number and where the reader (base 2, smartphone, or any other appropriate reading equipment) gets connected to the data server 4 to access a database memorizing, in an associated way, all the identification numbers and identities of their owners (for example family name/first name and in the case of living in a collective structure, the room number and floor).

After identification 411 of the owner of the retrieved dental prosthesis 1, it is imperative for reasons of hygiene to return to the state 412 of cleaning the dental prosthesis 1.

During the six-monthly visits to the prosthodontist (state 415) the latter removes the power cell 331 from the dental prosthesis 1 to change it. The used cell is recycled (state 417) and a new cell is inserted in the dental prosthesis (state 402) as a replacement for the used cell.

During these appointments, it is also possible for the prosthodontist to note that it is time to change the dental prosthesis: the prosthesis then passes into an end-of-life state 414. The power cell 331 and the embedded electronics in the prosthetic device 1 can then be recycled (state 413).

The invention claimed is:

1. A system of tracing a dental prosthesis, said system comprising:
   the dental prosthesis comprising;
   an electrical power source;
   a radio-communications signals transmitter coupled with the power source and configured to assume a weakly active state in which the transmitter periodically sends out signals at a first transmission frequency, and a highly active state in which the transmitter periodically sends out signals at a second transmission frequency, which is higher than the first transmission frequency; and at least one presence sensor configured to sense presence of the prosthesis in a mouth of a user, and to deliver a piece of information on the presence or absence of said prosthesis in said mouth, wherein said radio-communications signals transmitter is configured to pass from said weakly active state to said highly active state when said sensor delivers a piece of information on absence of the prosthesis in said mouth; and a base forming a support of said dental prosthesis when the dental prosthesis is not being worn by the user, and wherein said transmitter is configured to assume said weakly active state on detecting a presence of said dental prosthesis in proximity to said base.

2. The system according to claim 1 wherein, on detecting presence of said dental prosthesis in proximity to said base, said dental prosthesis is configured to operate in "base" mode in which said presence sensor is in an inactive state and in which said radio-communications signals transmitter is in the weakly active state.

3. The system according to claim 1 wherein, on detecting an absence of said dental prosthesis in proximity to said base, said dental prosthesis is configured to work in "recognition" mode in which said presence sensor carries out a measurement of presence at a determined frequency, and in which said radio-communications signals transmitter is in said weakly active state.

4. The system according to claim 1, wherein said transmitter is configured so that, when said sensor delivers a piece of information on absence of said prosthesis in said mouth, the transmitter passes from said weakly active state to said highly active state in which the transmitter is configured to periodically send out signals at the second transmission frequency, and wherein said base comprises a module configured to send a command for a mode of operation of said dental prosthesis to said dental prosthesis, upon action by the user, including a command for operation in "location" mode, in which said radio-communication signals transmitter is configured to periodically send out signals at a third transmission frequency, which is higher than the second transmission frequency.

5. The system according to claim 1, wherein said base comprises a warning module configured to send out an alert:
  when a duration of presence of said dental prosthesis in proximity to said base is greater than a determined threshold of presence, or
  when a duration of absence of said dental prosthesis in proximity to said base is greater than a determined threshold of absence.

6. The system according to claim 1, wherein said base comprises a unit for locating said dental prosthesis, comprising at least one directional antenna connected to a radio module for receiving radio-communications signals sent out by the transmitter of said dental prosthesis and a set of light indicators for controlling a direction of reception of said signals.

7. The system according to claim 1, wherein said base comprises a charger, which charges said electrical power source by induction.

8. The system according to claim 1, wherein said dental prosthesis comprises a passive radiofrequency identification label and said base comprises a radiofrequency identification label reader.

9. A dental prosthesis comprising;
  an electrical power supply source;
  a radio-communications signals transmitter coupled with the electrical power source and configured to assume a weakly active state in which the transmitter periodically sends out signals at a first transmission frequency and a highly active state in which the transmitter periodically sends out signals at a second transmission frequency, which is higher than the first frequency; and
  at least one presence sensor configured to sense presence in a user's mouth, and delivering a piece of information on presence or absence of said prosthesis in said mouth,
  wherein said transmitter is configured to pass from said weakly active state to said highly active state when said sensor delivers a piece of information on absence of said prosthesis in said mouth, and
  said transmitter is configured to assume said weakly active state on detecting a presence of said dental prosthesis in proximity to a base forming a support of said dental prosthesis when the dental prosthesis is not being worn by the user.

10. A method of tracing a dental prosthesis, comprising an electrical power source coupled with a radio-communications signals transmitter configured to assume a weakly active state in which the transmitter periodically sends out signals at a first transmission frequency, and a highly active state in which the transmitter periodically sends out signals at a second transmission frequency, which is higher than the first transmission frequency,
  wherein the method comprises the following acts performed by the dental prosthesis:
  sensing presence of said prosthesis in a mouth of a user using at least one presence sensor and supplying a piece of information on absence of said prosthesis in said mouth,
  upon receiving said piece of information on absence, passing from said weakly active state to said highly active state,
  detecting a presence of said dental prosthesis in proximity to a base forming a support of said dental prosthesis when the dental prosthesis is not being worn by the user,
  on detecting a presence of said dental prosthesis in proximity to said base, configuring said transmitter in said weakly active state.

* * * * *